United States Patent
Hwang et al.

(10) Patent No.: US 9,461,637 B2
(45) Date of Patent: Oct. 4, 2016

(54) METHOD AND APPARATUS FOR CONTROLLING A GATE VOLTAGE IN HIGH ELECTRON MOBILITY TRANSISTOR

(71) Applicant: Samsung Electronics Co., Ltd., Suwon-Si, Gyeonggi-Do (KR)

(72) Inventors: Sun-kyu Hwang, Seoul (KR); Woo-chul Jeon, Daegu (KR); Joon-yong Kim, Seoul (KR); Ki-yeol Park, Suwon-si (KR); Young-hwan Park, Seoul (KR); Jai-kwang Shin, Anyang-si (KR); Jae-joon Oh, Seongnam-si (KR); Jong-bong Ha, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 256 days.

(21) Appl. No.: 14/106,991

(22) Filed: Dec. 16, 2013

(65) Prior Publication Data
US 2014/0240026 A1    Aug. 28, 2014

(30) Foreign Application Priority Data
Feb. 26, 2013    (KR) .................. 10-2013-0020675

(51) Int. Cl.
  *H03K 17/06*    (2006.01)
  *H01L 29/778*   (2006.01)
  *H01L 29/20*    (2006.01)
  *G01N 27/02*    (2006.01)
  *G01N 27/08*    (2006.01)

(52) U.S. Cl.
  CPC ......... *H03K 17/063* (2013.01); *H01L 29/7787* (2013.01); *G01N 27/025* (2013.01); *G01N 27/08* (2013.01); *H01L 29/2003* (2013.01)

(58) Field of Classification Search
  CPC ............. H03K 17/063; H03K 17/687; H01L 29/7789; H01L 29/2003; H01L 29/7783; H01L 29/0692; H01L 29/7787

USPC ........ 324/713, 750.01; 257/187, 76, E27.06, 257/E31.082; 977/742, 954; 716/119; 361/79, 86; 327/416; 307/127; 320/128; 342/175; 323/224, 289, 283
See application file for complete search history.

(56) References Cited

U.S. PATENT DOCUMENTS

| | | | |
|---|---|---|---|
| 7,282,943 B2* | 10/2007 | Sakaguchi | G01R 31/2621 324/762.09 |
| 7,948,220 B2 | 5/2011 | Bahramian | |
| 9,077,336 B2* | 7/2015 | Imada | H03K 17/063 |
| 2005/0237046 A1* | 10/2005 | Sutardja | H02M 1/08 323/351 |
| 2007/0257725 A1* | 11/2007 | De | H03K 17/08128 327/379 |
| 2012/0275076 A1* | 11/2012 | Shono | H01M 10/48 361/86 |
| 2012/0293218 A1* | 11/2012 | Dewa | H03K 17/063 327/109 |
| 2013/0200908 A1* | 8/2013 | Huebschman | G01R 31/2621 324/750.01 |
| 2014/0062435 A1* | 3/2014 | Lu | H02J 7/0072 323/282 |

FOREIGN PATENT DOCUMENTS

| | | |
|---|---|---|
| JP | 2004-356548 A | 12/2004 |
| JP | 2007-188923 A | 7/2007 |
| KR | 10-0320448 B1 | 6/1994 |
| KR | 10-0782430 B1 | 12/2007 |

* cited by examiner

*Primary Examiner* — Benjamin M Baldridge
*Assistant Examiner* — Felicia Farrow
(74) *Attorney, Agent, or Firm* — Harness, Dickey & Pierce, P.L.C.

(57) ABSTRACT

According to example embodiments, a method for controlling a gate voltage applied to a gate electrode of a high electron mobility transistor (HEMT) may include measuring a voltage between a drain electrode and a source electrode of the HEMT, and adjusting a level of the gate voltage applied to the gate electrode of the HEMT according to the measured voltage. The level of the gate electrode may be adjusted if the voltage between the drain electrode and the source electrode is different than a set value.

19 Claims, 7 Drawing Sheets

METHOD AND APPARATUS FOR CONTROLLING A GATE VOLTAGE IN HIGH ELECTRON MOBILITY TRANSISTOR

CROSS-REFERENCE TO RELATED APPLICATIONS

This application claims priority under 35 U.S.C. §119 to Korean Patent Application No. 10-2013-0020675, filed on Feb. 6, 2013, in the Korean Intellectual Property Office, the disclosure of which is incorporated herein in its entirety by reference.

BACKGROUND

1. Field

The present disclosure relates to methods and/or apparatuses for controlling a gate voltage in a high electron mobility transistor (HEMT), and more particularly, to methods and/or apparatuses for controlling a gate voltage in a HEMT according to source-drain voltages.

2. Description of Related Art

Controlling a flow of currents via ON/OFF switching may be used to drive various motors or power transformation systems (AC to DC, DC to AC, and DC to DC).

To this end, a silicon-based switching devices, such as power metal oxide semiconductor field effect transistor (MOSFET), an insulated gate bipolar transistor (IGBT), a bipolar junction transistor (BJT), and a Schottky barrier diode (SBD), may be used. However, due to material limitations of silicon, efficiencies of the switching devices are limited.

As an attempt to overcome the material limits of silicon, research is being actively conducted in relation to a high electron mobility transistor (HEMT) using materials including gallium nitride (GaN).

However, in such a HEMT, ON resistance may increase during a high-voltage switching operation due to factors including charges formed between a drain and a gate, and thus current collapse may occur. Therefore, switching loss may increase in the HEMT.

SUMMARY

Example embodiments relate to methods and/or apparatuses for controlling a gate voltage of a high electron mobility transistor (HEMT), which are capable of reducing current collapse by measuring a voltage between a drain electrode and a source electrode of a switching HEMT and, if the voltage increases, increasing voltage of pulses applied to a gate.

Example embodiments relate to methods and/or apparatuses for controlling a gate voltage of a high electron mobility transistor (HEMT), which are capable of reducing a gate leakage current by measuring a voltage between a drain electrode and a source electrode of a switching HEMT and, if the voltage increases, decreasing voltage of pulses applied to a gate.

Additional aspects will be set forth in part in the description which follows and, in part, will be apparent from the description, or may be learned by practice of example embodiments.

According to example embodiments, a method of controlling a gate voltage applied to a gate electrode of a high electron mobility transistor (HEMT) includes: measuring a voltage between a drain electrode and a source electrode of the HEMT; and adjusting a level of the gate voltage applied to the gate electrode of the HEMT according to the measured voltage.

In example embodiments, if the voltage between the drain electrode and the source electrode is higher than a set value, the adjusting the level of the gate voltage may include increasing the level of the gate voltage applied to the gate electrode by a desired (and/or alternatively predetermined) value.

In example embodiments, the measuring of the voltage and the controlling of the gate voltage may be repeatedly performed until the voltage between the drain electrode and the source electrode reaches the set value.

In example embodiments, the set value of the voltage between the drain and source electrode at which current collapse in the HEMT is reduced.

In example embodiments, the HEMT may be a GaN-based field effect transistor (GaN-FET).

In example embodiments, the gate electrode of the HEMT may be a p-GaN type gate electrode.

In example embodiments, if the voltage between the drain electrode and the source electrode is lower than a set value, the adjusting the level of the gate voltage may include decreasing the level of the gate voltage applied to the gate electrode by a desired (and/or alternatively predetermined) value.

In example embodiments, the set value may be a value corresponding to an ON resistance that does not interfere with operation of the HEMT.

In example embodiments, the voltage between the drain electrode and the source electrode may be measured by using a resistance.

In example embodiments, the voltage between the drain electrode and the source electrode is measured by using a photodiode.

According to example embodiments, an apparatus for controlling a gate voltage applied to a gate electrode of a high electron mobility transistor (HEMT) includes: a voltage measuring unit configured to measure a voltage between a drain electrode and a source electrode of the HEMT; and a gate voltage controlling unit configured to adjust a level of the gate voltage applied to the HEMT according to the measured voltage.

BRIEF DESCRIPTION OF THE DRAWINGS

These and/or other aspects will become apparent and more readily appreciated from the following description of non-limiting embodiments, taken in conjunction with the accompanying drawings in which like reference characters refer to the same parts throughout the different views. The drawings are not necessarily to scale, emphasis instead being placed upon illustrating principles of example embodiments. In the drawings.

DETAILED DESCRIPTION

Figure 1:
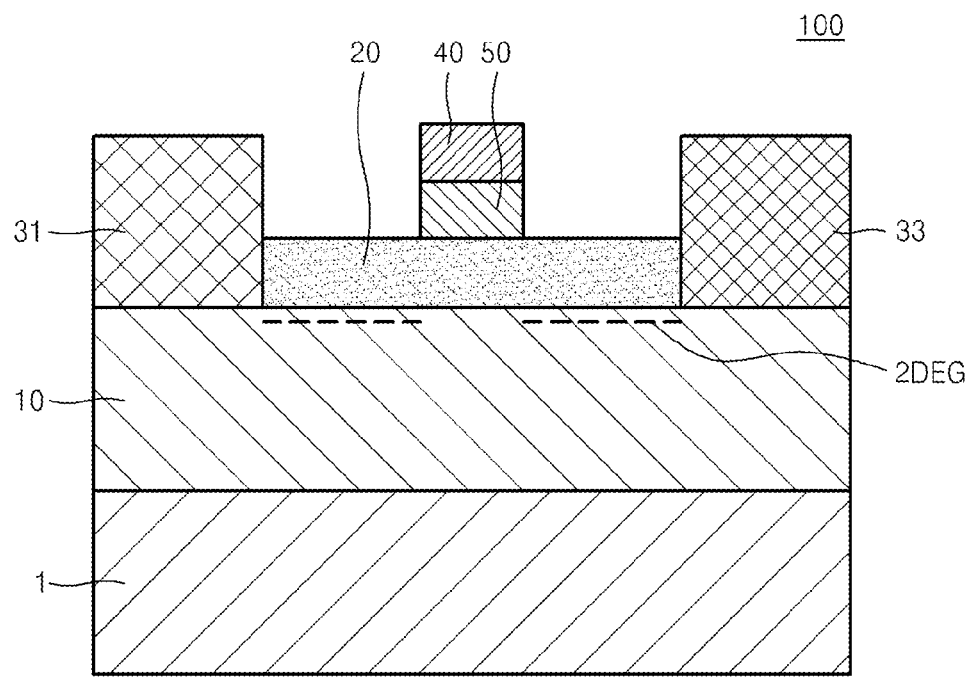
FIG. 1 is a schematic view of a high electron mobility transistor (HEMT) according to example embodiments.

Example embodiments will now be described more fully with reference to the accompanying drawings, in which some example embodiments are shown. Example embodiments, may, however, be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference numerals in the drawings denote like elements, and thus their description may be omitted.

Certain detailed explanations of related art are omitted when it is deemed that they may unnecessarily obscure the description of example embodiments.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof. Expressions such as "at least one of," when preceding a list of elements, modify the entire list of elements and do not modify the individual elements of the list.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a schematic view of a high electron mobility transistor (HEMT) 100 according to example embodiments.

Referring to FIG. 1, a HEMT 100 according to example embodiments may include a substrate 1, a channel layer 10 formed on the substrate 1, a channel supply layer 20 formed on the channel layer 10, a source electrode 31 and a drain electrode 33 formed on the channel layer 10, and a gate electrode 40 arranged between the source electrode 31 and the drain electrode 33. However, example embodiments are not limited to the structure shown in FIG. 1 and may correspond to any of various HEMTs having characteristics as described below.

Generally, the HEMT 100 includes semiconductor layers having different polarization characteristics. In the HEMT 100, a semiconductor layer having a relatively strong polarization characteristic may cause a 2-dimensional electron gas (referred to hereinafter as '2DEG') to be formed/generated at another semiconductor layer combined therewith via a hetero-junction. The 2DEG may be used as a channel between the drain electrode 33 and the source electrode 31, where a current flowing in the channel is controlled by a bias voltage applied to the gate electrode 40.

Figure 2:
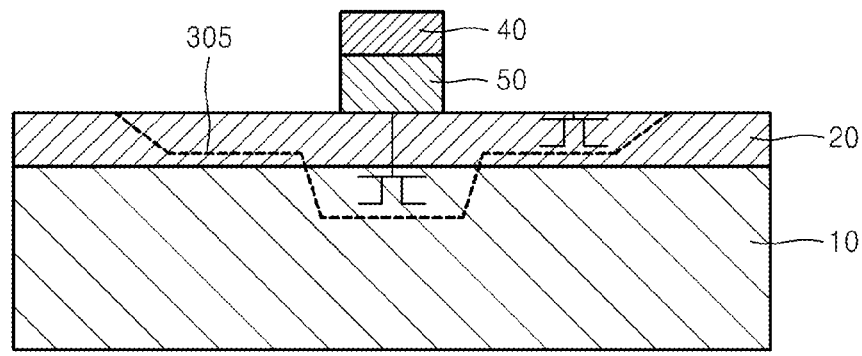
FIGS. 2 and 3 are sectional views showing expansion of a depletion layer when a voltage is applied to a drain electrode and are for describing the mechanism by which current collapse occurs.

The substrate 1 may be formed of sapphire, silicon (Si), silicon carbide (SiC), GaN, etc., but example embodiments are not limited thereto. Although not shown, a buffer layer may be interposed between the substrate 1 and the channel layer 10. The buffer layer may be provided to limit (and/or prevent) deterioration of crystallinity of the channel layer 10. The buffer layer may reduce differences in lattice constants and thermal expansion coefficients between the substrate 1 and the channel layer 10. The buffer layer includes a nitride containing at least one of Al, Ga, In, and B and may have a single-layer structure or a multi-layer structure. For example, the buffer layer may be formed of AlN, GaN, AlGaN, InGaN, AlInN, or AlGaInN, for example, and may have a single-layer structure or a multi-layer structure. The substrate 1 and the buffer layer may be removed after the HEMT 100 is formed as shown in FIG. 2. In other words, the substrate 1 and the buffer layer may be selectively arranged in the HEMT 100.

The channel layer 10 is formed on the substrate 1 and forms a channel between the source electrode 31 and the drain electrode 33. The channel layer 10 may be a nitride semiconductor layer. The channel layer 10 may be a layer containing GaN, InGaN, AlGaN, or a combination thereof, for example. However, the channel layer 10 is not limited thereto, and the channel layer 10 may be any of various other material layers as long as the 2DEG may be formed therein. The channel layer 10 may be an undoped layer. However, if necessary, the channel layer 10 may be doped with a desired (and/or alternatively predetermined) impurity.

The channel supply layer 20 may be arranged on the channel layer 10. The channel supply layer 20 may form the 2DEG in the channel layer 10. Here, the 2DEG may be formed in the portion of the channel layer 10 below the interface between the channel layer 10 and the channel supply layer 20. The channel supply layer 20 may contain a second semiconductor material that is different from a first semiconductor material in the channel layer 10.

The second semiconductor material may differ from the first semiconductor material with respect to at least one from among polarization characteristics, an energy bandgap, and a lattice coefficient. For example, at least one of the polarization characteristics and the energy bandgap of the second semiconductor material may be greater than that (those) of the first semiconductor material.

The channel supply layer 20 may include at least one nitride including at least one of Al, Ga, In, and B, for example, and may have a single-layer structure or a multi-layer structure. For example, the channel supply layer 20 may include at least one from among AlGaN, AlInN, InGaN, AlN, and AlInGaN. However, example embodiments are not limited thereto. The channel supply layer 20 may be an undoped layer or a layer doped with a desired (and/or alternatively predetermined) impurity. A thickness of the channel supply layer 20 may be up to dozens of nm. For example, the thickness of the channel supply layer 20 may be less than or equal to 50 nm. However, example embodiments are not limited thereto.

The source electrode 31 and the drain electrode 33 may be arranged on portions of the channel layer 10 at two opposite ends of the channel supply layer 20. Here, the source electrode 31 and the drain electrode 33 may be electrically connected to the 2DEG. The source electrode 31 and the drain electrode 33 may be arranged on the channel supply layer 20 and may extend into the channel supply layer 20 or into the channel layer 10. Configurations of the source electrode 31 and the drain electrode 33 may differ in various ways.

A depletion forming layer 50 having a desired (and/or alternatively predetermined) thickness may be formed on the portion of the channel supply layer 20 between the source electrode 31 and the drain electrode 33. Here, the depletion forming layer 50 may form a depletion layer in the 2DEG. Due to the depletion forming layer 50, an energy bandgap of the portion of the channel supply layer 20 below the depletion forming layer 50 may increase, and thus 2DEG depletion layer may be formed at the portion of the channel layer 10 corresponding to the depletion forming layer 50. Therefore, a portion of the 2DEG corresponding to the depletion forming layer 50 may be blocked or may have different characteristics (e.g., electron concentration) from the remaining of the 2DEG. The region at which the 2DEG is blocked may be referred to as a 'blocked region,' and, due to the blocked region, the HEMT 100 may have a normally-off characteristic. In other words, unless a voltage exceeding a threshold voltage is applied to the gate electrode 40, 2DEG is kept being blocked between the source electrode 31 and the drain electrode 33, and thus a current does not flow therein.

The depletion forming layer 50 may include a p-type semiconductor material. In other words, the depletion forming layer 50 may be a p-type semiconductor layer or a semiconductor layer doped with a p-type impurity. Furthermore, the depletion forming layer 50 may include a Group III-V nitride semiconductor. For example, the depletion forming layer 50 may include at least one from among GaN, AlGaN, InN, AlInN, InGaN, and AlInGaN and may be doped with a p-type impurity, such as Mg. For example, the depletion forming layer 50 may be a p-GaN layer or a p-AlGaN layer. Due to the depletion forming layer 50, an energy bandgap of the portion of the channel supply layer 20 therebelow increases, and thus a 2DEG depletion layer may be formed. However, the depletion forming layer 50 is not limited thereto and may be formed in any of various shapes.

The gate electrode 40 may be arranged on the depletion forming layer 50. The gate electrode 40 may include various metals or metal compounds. Here, the gate electrode 40 may have a same width as the depletion forming layer 50. Meanwhile, the gate electrode 40 may have a greater width than the depletion forming layer 50. The gate electrode 40 may be arranged closer to the source electrode 31 than to the drain electrode 33. However, this is merely an example, and the location of the gate electrode 40 may vary.

A switching device according to example embodiments as described above may overcome limits in material properties and a manufacturing process regarding silicon and may further improve efficiency of a power device.

However, in such a HEMT transistor, ON resistance increases during a high-voltage switching operation due to factors including charges formed between a drain and a gate, and thus current collapse may occur. Therefore, switching loss may increase in the HEMT. Particularly, the current collapse significantly increases ON resistance, thus being a serious problem in a power transistor to which high drain voltage is applied. Detailed descriptions thereof will be given below with reference to FIGS. 2 and 3.

Figure 3:
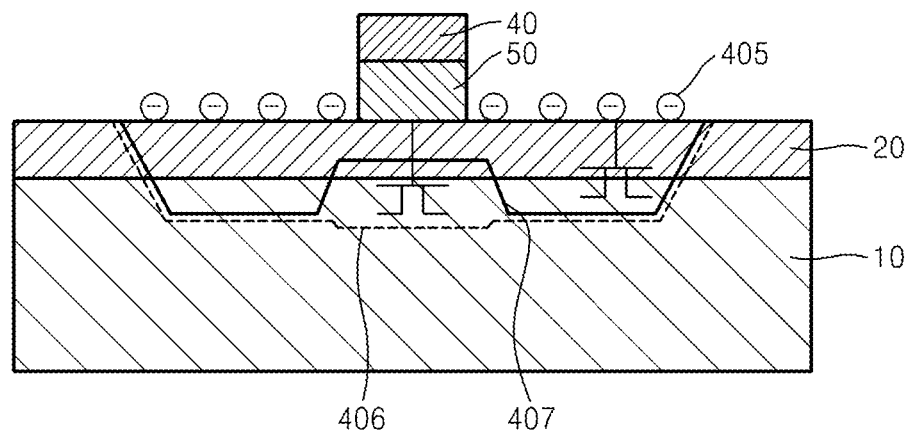

FIGS. 2 and 3 are sectional views showing expansion of a depletion layer when a voltage is applied to a drain electrode and are for describing the mechanism by which current collapse occurs.

Referring to FIG. 2, if a low drain voltage from about 1V to about 2V is applied during an OFF state (gate electrode voltage is 0 V or −1 V), a depletion layer may appear as indicated by the reference numeral 305 due to an effect of the depletion forming layer 50 described above.

Referring to FIG. 3, if a high drain voltage of about 60 V is applied during the OFF state, a depletion layer expands. That is, the depletion layer depletion layer 406 larger than the depletion layer 305 of FIG. 2 is formed next to the gate electrode 40. Here, the depletion layer 406 may be formed next to the gate electrode 40 and may be identical to a depletion layer 407 formed next to the gate electrode 40 during an ON state.

When the 60V drain voltage is applied during the OFF state, if a 3 V voltage is applied to the gate electrode 40, a depletion layer is affected by electrons 405 trapped on a surface of the channel supply layer 20 and is changed from the OFF-state depletion layer 406 to the ON-state depletion layer 407. In other words, since discharge of electrons trapped on a surface of the channel supply layer 20 may be delayed, the depletion layer 407 next to the gate electrode 40 may stay expanded, where a drain-source current does not increase. In other words, although gate electrode voltage increases, ON resistance increases, and thus a desired (and/or maximum) amount of current decreases. This phenomenon is referred to as current collapse.

Figure 4:
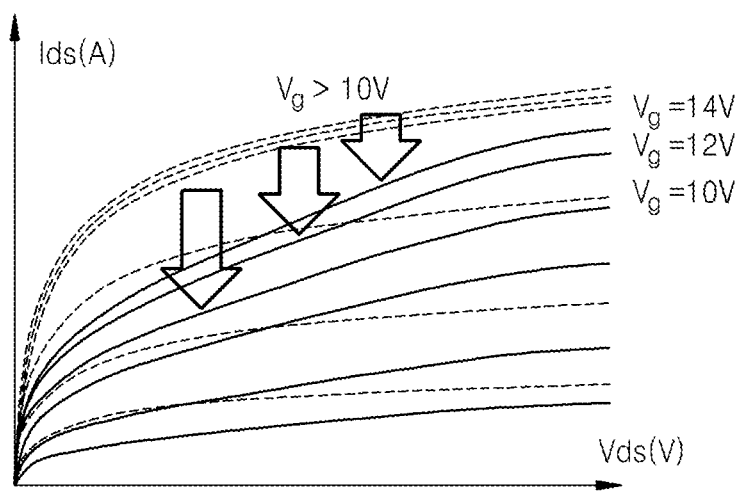
FIG. 4 is a graph showing Ids-Vds changes according to an occurrence of current collapse.

FIG. 4 is a graph showing Ids-Vds changes according to an occurrence of current collapse.

Referring to FIG. 4, the graph indicated as a dotted line indicates voltage Vds and current Ids between a drain electrode and a source electrode according to gate voltages when current collapse does not occur, whereas the graph indicated as a solid line indicates voltage Vds and current Ids between a drain electrode and a source electrode according to gate voltages when current collapse occurs.

If the HEMT 100 is switched when a low voltage is applied between a drain electrode and a source electrode, a current Ids between the drain electrode and the source electrode tends to increase at a same Vds in proportion to a gate voltage until the gate voltage reaches 10 V, as indicated by the dotted line in FIG. 4. Once the gate voltage exceeds 10 V, the current Ids is saturated. Therefore, even if the gate voltage increases, the current between the drain electrode and the source electrode does not increase any more.

However, as described above, if the HEMT 100 is switched when a high voltage is applied between the drain electrode and the source electrode, current collapse may occur, and the graph may have a different form. For example, as indicated by the solid line in FIG. 4, if the HEMT 100 is switched when a high voltage is applied between the drain electrode and the source electrode, a relatively low current flows even if a gate voltage that is the same as that in the low-voltage switching is applied. Furthermore, even if the gate voltage exceeds 10 V, which is the saturation voltage in the low-voltage switching, the current Ids is not saturated. The reason for this is that, since current collapse occurs during high-voltage switching of the HEMT 100, ON resistance temporarily increases.

Meanwhile, referring to FIG. 4, if the HEMT 100 is switched (solid line) when a high voltage is applied between a drain electrode and a source electrode of the HEMT 100, a current Ids between the drain electrode and the source electrode increases as the gate voltage increases. The reasons for this is that, as described above with reference to FIG. 3, a depletion layer that has expanded as a high voltage is applied to the drain electrode may be made to contract by relatively increasing a gate voltage.

Therefore, according to example embodiments, a method and an apparatus for controlling a gate voltage with reduced loss by limiting (and/or preventing) current collapse by relatively increasing a gate voltage during high-voltage switching may be provided based on the characteristics of the HEMT 100.

Figure 5:
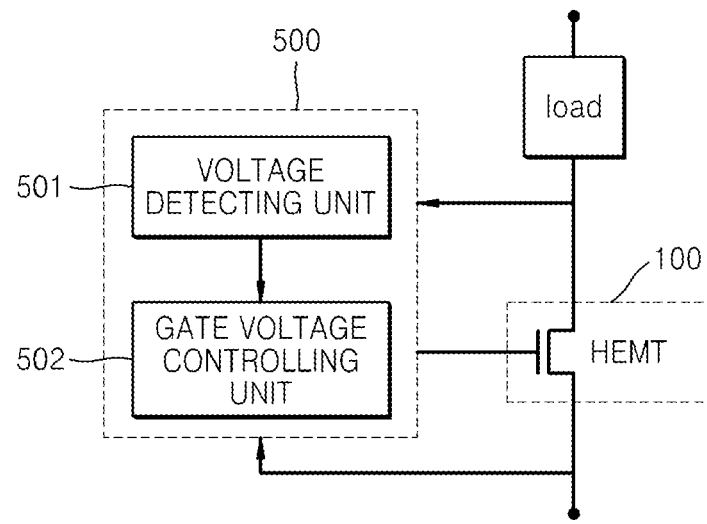
FIG. 5 is a schematic view of a gate voltage adjusting device of the HEMT, according to example embodiments.

FIG. 5 is a schematic view of a gate voltage adjusting device 500 of the HEMT 100, according to example embodiments.

Referring to FIG. 5, the gate voltage adjusting device 500 of the HEMT 100 may include a voltage detecting unit 501 for detecting a voltage Vds between a drain electrode and a source electrode and a gate voltage controlling unit 502.

First, the voltage detecting unit 501 is connected to both ends of a drain electrode and a source electrode of the HEMT 100 and measures a voltage between the drain electrode and the source electrode. The voltage may be measured by using a method using a resistance, a method using photodiode coupling, etc., but is not limited thereto.

Next, the measured voltage is transmitted to the gate voltage controlling unit 502, and, if the voltage between the drain electrode and the source electrode is higher than a set value, current collapse may be reduced by increasing a gate voltage as described below.

Here, the set value is a value at which it may be considered that current collapse in the HEMT 100 is reduced, and the set value may be set based on experiments or experiences of a designer according to device characteristics of the HEMT 100. Furthermore, the gate voltage may be controlled by applying changed voltages step-by-step. Alternatively, the gate voltage may be changed in a linear fashion.

Figure 6:
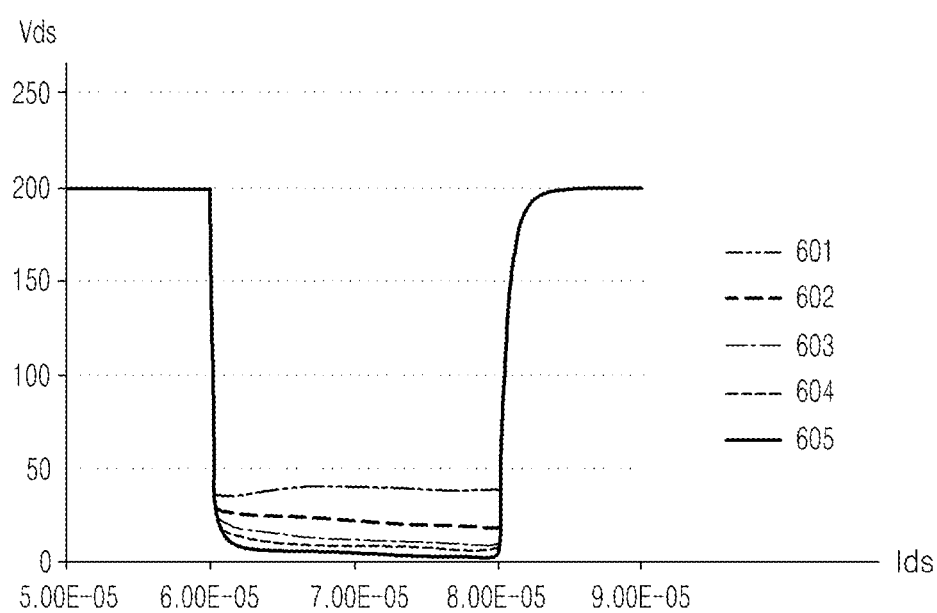
FIG. 6 is a graph showing a result of measuring reduction of current collapse according to increase of a gate voltage, according to example embodiments.

FIG. 6 is a graph showing a result of measuring reduction of current collapse according to an increase in a gate voltage, according to example embodiments.

FIG. 6 shows a graph obtained by applying a 200 V voltage to a drain electrode during an OFF state of the HEMT 100 and measuring drain voltages by changing the gate voltage to a 10 V voltage 601, a 12 V voltage 602, a 14 V voltage 603, a 16 V voltage 604, and an 18 V voltage 606 in the order stated.

In FIG. 6, since the voltage between the drain electrode and the source electrode is relatively high at the gate voltage 601, it is likely that current collapse occurs at the gate voltage 601. This is a problem of the conventional HEMT when a high voltage is applied to a drain electrode. However, as shown in FIG. 6, as the gate voltage increases (from 601 to 605), the voltage between the drain electrode and the source electrode is more and more lower than 601. That is, ON resistance decreases, and thus loss due to current collapse decreases. Particularly, if the set value of the voltage between the drain electrode and the source electrode is set to 5 V or lower, the gate voltage adjusting device 500 of the HEMT 100 according to example embodiments may control the gate voltage to be maintained higher than the gate voltage 604, which is 16 V, and thus the effect of current collapse may be reduced.

In other words, according to example embodiments, current collapse in GaN power devices including a 2DEG may be reduced by controlling gate voltages as described above.

Figure 7:
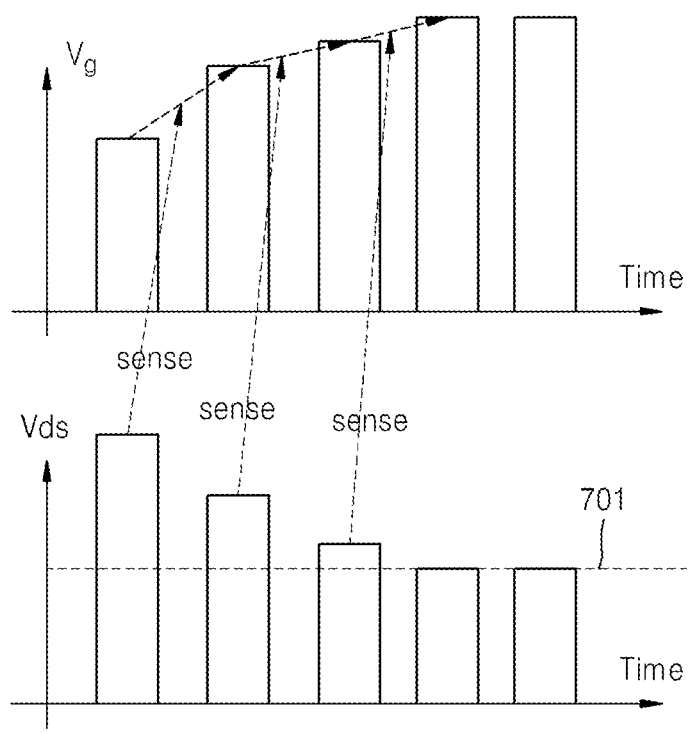
FIG. 7 is a bar graph showing a process for detecting a voltage between a drain electrode and a source electrode and reducing current collapse by increasing a gate voltage, according to example embodiments.

FIG. 7 is a bar graph showing a process for detecting a voltage between a drain electrode and a source electrode and reducing current collapse by increasing a gate voltage, according to example embodiments.

Referring to FIG. 7, it is determined whether the voltage between the drain electrode and the source electrode is higher than a set value 701 as described above, and, if the voltage between the drain electrode and the source electrode is higher than the set value 701, the voltage between the drain electrode and the source electrode may be reduced by gradually increasing a gate voltage. Here, a cycle of determining whether the voltage between the drain electrode and the source electrode is higher than the set value and a value by which the gate voltage is increased may be selectively set by a designer arbitrarily or based on his or her experience.

Meanwhile, an increase in a gate voltage does not only cause a decrease in current collapse, but also has demerits. For example, if a gate voltage increases, power loss at a gate may increase, and stability and reliability of operation of a HEMT may be deteriorated. Particularly, in a case where a p-GaN type gate is used, excessive current may be applied to a gate during an ON operation as a gate voltage increases. Therefore, a gate leakage current may be reduced by lowering a gate voltage without interfering with operation of system which comprises the HEMT 100, even if ON resistance increases by a desired (and/or alternatively predetermined) value In other words, if a voltage between a drain electrode and a source electrode is lower than a set value, the gate leakage current may be reduced by increasing the voltage between the drain electrode and the source electrode by lowering a gate voltage. Here, the gate voltage is lowered within a scope not interfering operation of the system even if slight current collapse occurs.

Figure 8:
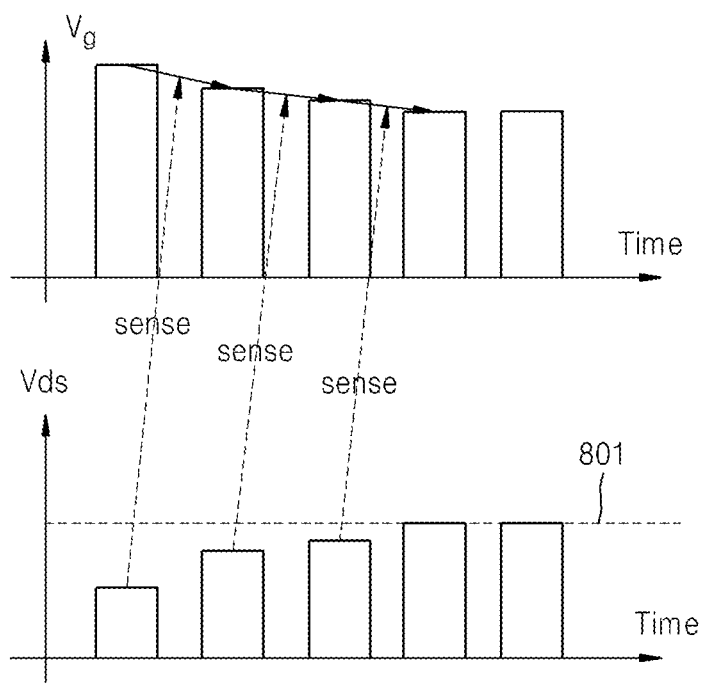
FIG. 8 is a bar graph showing a process for detecting a voltage between a drain electrode and a source electrode and reducing a gate leakage current by lowering a gate voltage.

FIG. 8 is a bar graph showing a process for detecting a voltage between a drain electrode and a source electrode and reducing a gate leakage current by lowering a gate voltage.

Referring to FIG. 8, it is determined whether the voltage between the drain electrode and the source electrode is lower than a set value 801, and, if the voltage between the drain electrode and the source electrode is lower than the set value 801, a gate voltage may be gradually reduced, thereby increasing the voltage between the drain electrode and the source electrode. Here, a cycle of determining whether the voltage between the drain electrode and the source electrode is higher than the set value and a value by which the gate voltage is increased may be selectively set by a designer arbitrarily or based on his or her experience.

Referring back to FIG. 5, the gate voltage controlling unit 502 according to example embodiments may be embodied as an integrated circuit (IC), a programmable logic controller (PLC), or any of various devices capable of controlling a gate voltage according to a voltage between a drain electrode and a source electrode detected by the voltage detecting unit 501 as described above, e.g., a processing device that is embodied by collecting calculating units, such as an arithmetic logic unit (ALU), a register, a program counter, a command decoder, and a control circuit, and a control device on a small silicon chip.

According to example embodiments, the voltage detecting unit 501 and the gate voltage controlling unit 502 may be integrated as a single unit or may be independent units. One of ordinary skill in the art will understand that the configuration of the gate voltage adjusting device 500 is not limited to the configuration described above.

Figure 9:
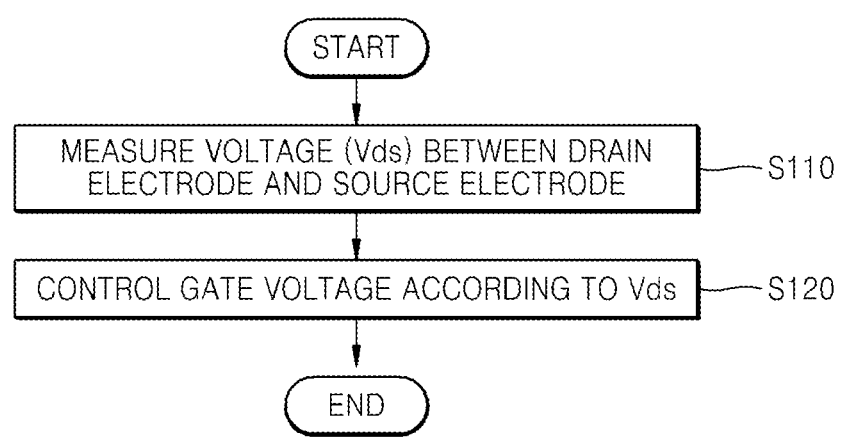
FIG. 9 is a flowchart showing a method of controlling a gate voltage of a HEMT according to example embodiments.

FIG. 9 is a flowchart showing a method of controlling a gate voltage of a HEMT 100, according to example embodiments.

Referring to FIG. 9, a voltage Vds between a drain electrode and a source electrode of the HEMT 100 is measured in operation S110. When the voltage Vds is measured, the method proceeds to operation S120 and current collapse is reduced or a gate leakage current is reduced by controlling a gate voltage according to the measured voltage Vds between the drain electrode and the source electrode.

Figure 10:
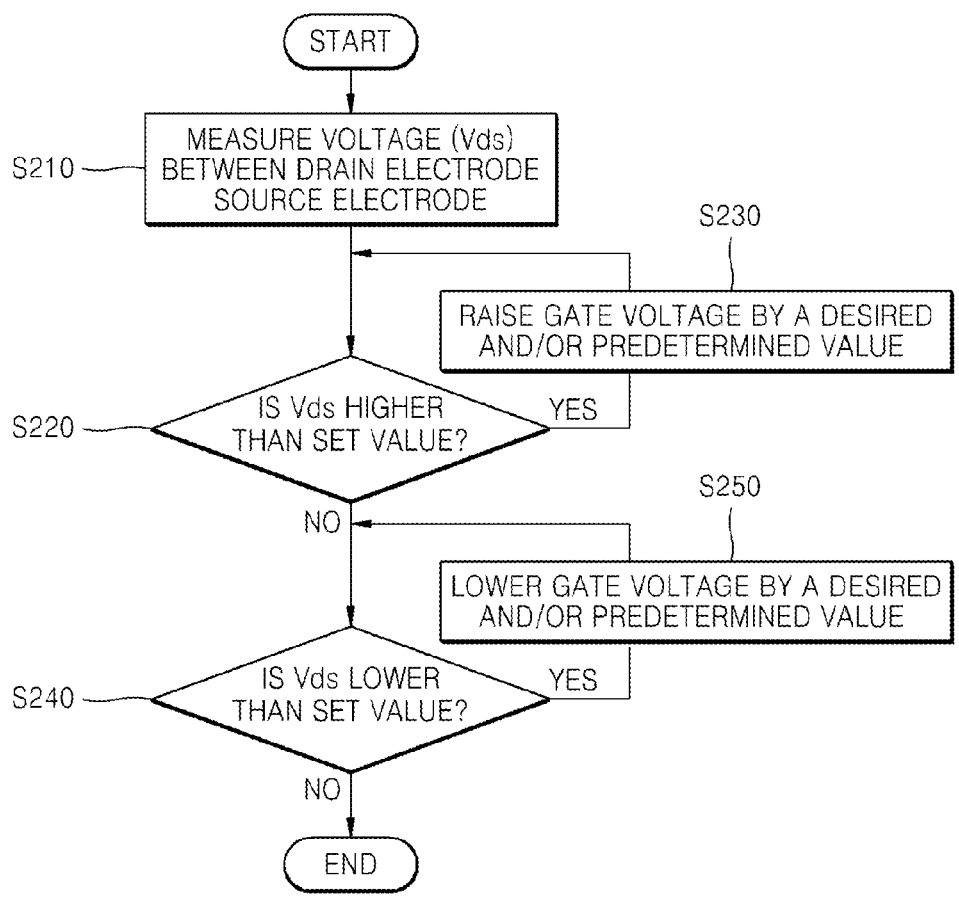
FIG. 10 is a flowchart showing a method of controlling a gate voltage of a HEMT according to example embodiments.

FIG. 10 is a flowchart showing a method of controlling a gate voltage of a HEMT 100, according to example embodiments.

Referring to FIG. 10, a voltage Vds between a drain electrode and a source electrode of the HEMT 100 is measured in operation S210. When the voltage Vds is measured, the method proceeds to operation S220 and it is determined whether the voltage Vds between the drain electrode and the source electrode is higher than a set value. If the voltage Vds between the drain electrode and the source electrode is higher than the set value, it is considered that current collapse is occurring. In this case, the method proceeds to operation S230 and a gate voltage is increased by a desired (and/or alternatively predetermined) value. Next, the method proceeds back to the operation S220. In this regard, current collapse may be reduced by repeating operations S220 and S230 until the voltage Vds between the drain electrode and the source electrode is no longer higher than the set value.

Here, the set value is a value at which it may be considered that current collapse in the HEMT 100 is reduced, and the set value may be set to a value at which it may be considered that current collapse in the HEMT 100 is reduced to a level that does not interfere with operation of the HEMT 100, based on experiments or experiences of a designer according to device characteristics of the HEMT 100. Furthermore, the desired (and/or alternatively predetermined) value of changing a gate voltage in a case where it is determined that current collapse is occurring may also be set to a value for easily adjusting the gate voltage to a set value for reducing the current collapse without significantly affecting system operation, based on experiments or experiences of a designer according to device characteristics of the HEMT 100.

Meanwhile, if the voltage Vds between the drain electrode and the source electrode is not higher than the set value, the method proceeds to an operation S240 and it is determined again whether the voltage Vds between the drain electrode and the source electrode is lower than a set value. Here, the set value in the operation S240 may be the same as or different from the set value in operation S220 and is a value set without interfering operation of system even if ON resistance increases by a desired (and/or alternatively predetermined) value. If the voltage Vds between the drain electrode and the source electrode is lower than the set value, it is considered that there is a large gate leakage current. In this case, the method proceeds to operation S250 and a gate voltage is reduced by a desired (and/or alternatively predetermined) value. Next, the method proceeds back to operation S240. In this regard, a gate leakage current may be reduced by repeating operations S240 and S250 until the voltage Vds between the drain electrode and the source electrode is no longer lower than the set value.

According to example embodiments, operations S240 and S250 may only be applied to the HEMT 100 employing a p-GaN type gate.

Accordingly, current collapse or a gate leakage current in the HEMT 100 during high-voltage switching may be reduced by controlling a gate voltage according to a measured voltage between a drain electrode and a source electrode.

The HEMT 100 described above with reference to the attached drawings may be used as a power device, for example. However, application of the HEMT 100 according to example embodiments is not limited thereto and may vary. In other words, the HEMT 100 according to example embodiments may not only be used as a power device, but also for various other purposes.

Figure 11:
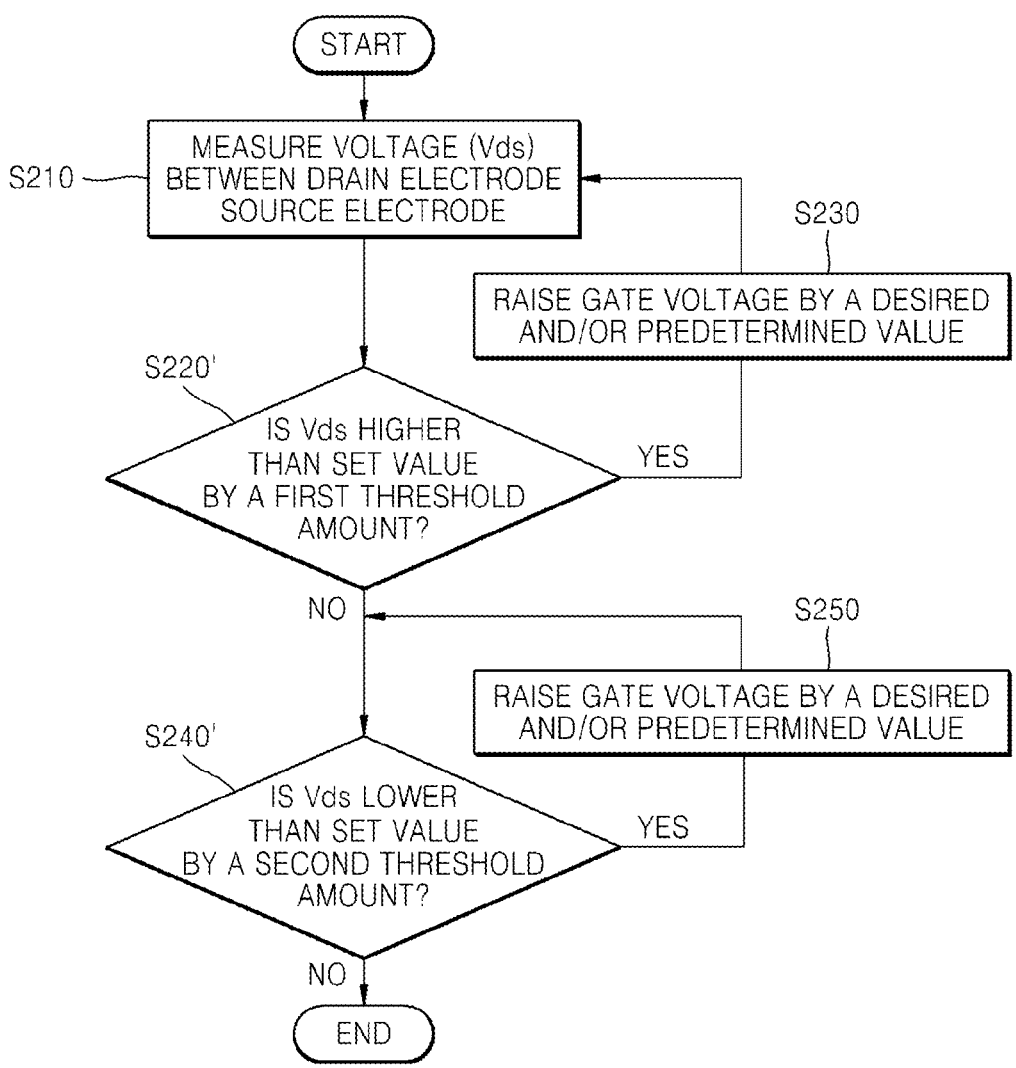
FIG. 11 is a flowchart showing a method of controlling a gate voltage of a HEMT according to example embodiments.

FIG. 11 is a flowchart showing a method of controlling a gate voltage of a HEMT according to example embodiments.

Referring to FIG. 11, operation S210 is the same as operation S210 described previously in FIG. 10. When the voltage Vds is measured, the method in FIG. 11 proceeds to operation S220' and the gate voltage adjusting device 500 (see FIG. 5) may determine whether the voltage Vds between the drain electrode and the source electrode is higher than a set value by a first threshold amount. If the voltage Vds is higher than the set value by a first threshold amount, the method proceeds to operation S230 and the gate voltage controlling unit 502 (see FIG. 5) may raise the gate voltage by a desired and/or predetermined value and then operation S220' is repeated. If the voltage Vds is not higher than the set value by a first threshold amount, then the method may proceed to operation S240' and the gate voltage adjusting device 500 may determine whether the voltage Vds between the drain electrode and the source electrode is lower than the set value by a second threshold amount. If the voltage Vds is lower than the set value by a second threshold amount, the method proceeds to operation S250 and the gate voltage controlling unit 502 (see FIG. 5) may lower the gate voltage by a desired and/or predetermined value and then operation S240' is repeated. In operation S240', if the voltage Vds is not lower than the set value by a second threshold amount, then method may proceed to the end. The first threshold amount and the second threshold amount may be the same or different.

Descriptions of features or aspects within each HEMT according to example embodiments should typically be considered as available for other similar features or aspects in other HEMTs according to example embodiments. For example, one of ordinary skill in the art will understand that various modifications may be made in the structure of the HEMT 100 shown in the attached drawings. For example, one of ordinary skill in the art will understand that materials other than GaN-based materials may be used for forming the channel layer 10 and the channel supply layer 20. Furthermore, one of ordinary skill in the art will understand that locations of the channel layer 10 and the channel supply layer 20 may be reversed. Furthermore, one of ordinary skill in the art will understand that example embodiments may also be applied to semiconductor devices other than the HEMT 100.

As described above, according to example embodiments, during high-voltage switching, a voltage between a drain electrode and a source electrode of a HEMT is measured, and, if the measured voltage is higher than a set value, voltage of pulses applied to a gate is increased to reduce current collapse, thereby reducing switching loss.

According to example embodiments, a voltage between a drain electrode and a source electrode of a p-GaN type HEMT is measured and, if the measured voltage is lower than a set value, voltage of pulses applied to a gate is decreased to reduce a gate leakage current.

The particular implementations shown and described herein should be understood in a descriptive sense only and not for purposes of limitation. For the sake of brevity, conventional electronics, control systems, software development and other functional aspects of the systems (and components of the individual operating components of the systems) may not be described in detail. Furthermore, the connecting lines, or connectors shown in the various figures presented are intended to represent examples of functional relationships and/or physical or logical couplings between the various elements. It should be noted that many alternative or additional functional relationships, physical connections or logical connections may be present in a practical device. Moreover, no item or component is essential to the practice of example embodiments unless the element is specifically described as "essential" or "critical".

While some example embodiments have been particularly shown and described, it will be understood by one of ordinary skill in the art that variations in form and detail may be made therein without departing from the spirit and scope of the claims.

What is claimed is:

1. A method of controlling a gate voltage applied to a gate electrode of a high electron mobility transistor (HEMT), the method comprising:
    measuring a voltage between a drain electrode and a source electrode of the HEMT; and
    adjusting a level of the gate voltage applied to the gate electrode of the HEMT according to the measured voltage;
    wherein, if the measured voltage between the drain electrode and the source electrode is higher than a set value, the adjusting the level of the gate voltage includes increasing the level of the gate voltage applied to the gate electrode until the voltage between the drain electrode and the source electrode reaches the set value,
    wherein the set value is a voltage level between the drain electrode and the source electrode at which current collapse in the HEMT is reduced.

2. The method of claim 1, wherein the adjusting the level of the gate voltage includes increasing the level of the gate voltage applied to the gate electrode by a desired value; and
    wherein the measuring of the voltage and the adjusting the level of the gate voltage are repeatedly performed until the voltage between the drain electrode and the source electrode reaches the set value.

3. The method of claim 1, wherein the set value is a value of the voltage between the drain and source electrode at which current collapse in the HEMT is reduced.

4. The method of claim 1, wherein the set value and the desired value may be set by a user.

5. The method of claim 1, wherein the HEMT is a GaN-based field effect transistor (GaN-FET).

6. The method of claim 1, wherein the gate electrode of the HEMT is a p-GaN type gate electrode.

7. The method of claim 6, wherein, if the voltage between the drain electrode and the source electrode is lower than the set value, the adjusting the level of the gate voltage includes decreasing the level of the gate voltage applied to the gate electrode by a desired value.

8. The method of claim 7, wherein the set value is a value corresponding to an ON resistance that does not interfere with operation of the HEMT.

9. The method of claim 1, wherein the measuring the voltage between the drain electrode and the source electrode includes measuring by using a resistance.

10. The method of claim 1, wherein the measuring the voltage between the drain electrode and the source electrode includes measuring by using a photodiode.

11. An apparatus for controlling a gate voltage applied to a gate electrode of a high electron mobility transistor (HEMT), the apparatus comprising: a voltage measuring unit configured to measure a voltage between a drain electrode and a source electrode of the HEMT; and a gate voltage controlling unit configured to adjust a level of the gate voltage applied to the gate electrode of the HEMT according to the measured voltage; wherein if the measured voltage between the drain electrode and the source electrode is higher than a set value the gate voltage controlling unit is configured to increase the level of the gate voltage applied to the gate electrode until the voltage between the drain electrode and the source electrode reaches the set value, wherein the set value is a voltage level between the drain electrode and the source electrode at which current collapse in the HEMT is reduced.

12. The apparatus of claim 11, wherein the gate voltage controlling unit is configured to increase the level of the gate voltage applied to the gate electrode by a desired value.

13. The apparatus of claim 11, wherein the HEMT is a GaN-based field effect transistor (GaN-FET).

14. The apparatus of claim 11, wherein the gate electrode of the HEMT is a p-GaN type gate electrode.

15. The apparatus of claim 14, wherein the gate voltage controlling unit is configured to decrease the level of the gate voltage applied to the gate electrode by a desired value if the voltage between the drain electrode and the source electrode is lower than the set value.

16. The apparatus of claim 11, wherein the voltage measuring unit is configured to measure the voltage between the drain electrode and the source electrode by using a resistance.

17. The apparatus of claim 11, wherein the voltage measuring unit is configured to measure the voltage between the drain electrode and the source electrode by using a photodiode.

18. The apparatus of claim 11, wherein the voltage measuring unit and the gate voltage controlling unit are independent units.

19. The apparatus of claim 11, wherein the apparatus is configured to operate during high-voltage switching of a power device.

* * * * *